United States Patent
Akhter et al.

(10) Patent No.: US 12,109,349 B2
(45) Date of Patent: Oct. 8, 2024

(54) METHODS, APPARATUSES, AND SYSTEMS FOR ASPIRATING AIRWAYS

(71) Applicant: The Board of Regents of the University of Texas System, Austin, TX (US)

(72) Inventors: Forhad Akhter, San Antonio, TX (US); Austin R. Schoppe, San Antonio, TX (US); Omar Navarro, San Antonio, TX (US); Bruce Adams, San Antonio, TX (US); Yusheng Feng, San Antonio, TX (US); Robert Delorenzo, San Antonio, TX (US); Robert L. Hood, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 796 days.

(21) Appl. No.: 17/286,404

(22) PCT Filed: Oct. 18, 2019

(86) PCT No.: PCT/US2019/057008
§ 371 (c)(1),
(2) Date: Apr. 16, 2021

(87) PCT Pub. No.: WO2020/081981
PCT Pub. Date: Apr. 23, 2020

(65) Prior Publication Data
US 2021/0386924 A1    Dec. 16, 2021

Related U.S. Application Data

(60) Provisional application No. 62/747,520, filed on Oct. 18, 2018.

(51) Int. Cl.
*A61M 1/00*    (2006.01)

(52) U.S. Cl.
CPC ............ *A61M 1/74* (2021.05); *A61M 1/60* (2021.05); *A61M 1/73* (2021.05); *A61M 1/76* (2021.05);
(Continued)

(58) Field of Classification Search
CPC ........... A61M 1/60; A61M 1/71; A61M 1/73; A61M 1/732; A61M 1/74; A61M 1/76;
(Continued)

(56) References Cited

U.S. PATENT DOCUMENTS

| 5,488,949 A | 2/1996 | Kreifels et al. |
| 5,642,730 A | 7/1997 | Baran |

(Continued)

OTHER PUBLICATIONS

Calkins, M.D. "Evaluation of possible battlefield suction pumps for the far-forward setting." *Military medicine* 2002, 167(10), 803-809.
(Continued)

*Primary Examiner* — Shefali D Patel

(57) ABSTRACT

The present disclosure includes methods, apparatuses, and systems for aspirating an airway of a patient. The apparatuses include a main body having a pump and a storage canister housing coupled to the main body and containing a storage container that is at least partially collapsible. In some configurations, the main body can include a pressure sensor, a controller in communication with the pressure sensor, and having a processor, a memory, and a power source in communication with the controller. The storage canister housing can include a first end coupled to the main body, and a second end having a weighted portion and configured to be coupled to the first end to permit free rotation, such that the second end gravitationally rotates.

20 Claims, 20 Drawing Sheets

(52) U.S. Cl.
CPC .............. *A61M 1/774* (2021.05); *A61M 1/79* (2021.05); *A61M 1/80* (2021.05); *A61M 1/84* (2021.05); *A61M 1/842* (2021.05); *A61M 1/86* (2021.05); *A61M 2205/3331* (2013.01); *A61M 2205/50* (2013.01); *A61M 2205/587* (2013.01); *A61M 2205/7545* (2013.01); *A61M 2210/1025* (2013.01)

(58) Field of Classification Search
CPC .......... A61M 1/77; A61M 1/774; A61M 1/79; A61M 1/80; A61M 1/84; A61M 1/842; A61M 1/86; A61M 1/87; A61M 1/88; A61M 1/884; A61M 2039/0009; A61M 2202/0014; A61M 2202/0028; A61M 2202/0042; A61M 2202/04; A61M 2202/0413; A61M 2202/06; A61M 2205/0238; A61M 2205/33; A61M 2205/3327; A61M 2205/3331; A61M 2205/3344; A61M 2205/50; A61M 2205/52; A61M 2205/58; A61M 2205/587; A61M 2205/75; A61M 2205/7545; A61M 2205/82; A61M 2205/8206; A61M 2210/1025; A61M 39/08; A61M 39/10; A61M 39/1055
See application file for complete search history.

(56) References Cited

U.S. PATENT DOCUMENTS

| | | |
|---|---|---|
| 2009/0281454 A1 | 11/2009 | Baker et al. |
| 2015/0126927 A1 | 5/2015 | Flickinger |
| 2015/0190598 A1 | 7/2015 | Hashimoto et al. |

OTHER PUBLICATIONS

Champion et al., "A profile of combat injury" *J Trauma* 2003, 54(5):S13-S19.

Eastridge et al., "Death on the battlefield (2001-2011): Implications for the future of combat casualty care" *J Trauma & Acute Care Surg* 2012, 73(6), S431-S437.

International Search Report and Written Opinion issued in Corresponding PCT Application No. PCT/US2019/057008, dated Dec. 26, 2019.

Peake, JB. "Beyond the Purple Heart: continuity of care for the wounded in Iraq" *N Engl J Med* 2005, 352(3):219-222.

Prokakis, et al. "Airway trauma: A review on epidemiology, mechanisms of injury, diagnosis and treatment" *Journal of Cardiothoracic Surgery* 2014, 9(1):117, 8 pages.

Simpson, A.T. "Transporting lazarus: Physicians, the state, and the creation of the modern paramedic and ambulance 1955-73." *History of Medicine & Allied Sciences* 2013, 68(2), 163-197.

METHODS, APPARATUSES, AND SYSTEMS FOR ASPIRATING AIRWAYS

This application is a national phase application under 35 U.S.C. § 371 of International Application No. PCT/US2019/057008, filed Oct. 18, 2019, which claims priority to U.S. Provisional Patent Application Ser. No. 62/747,520 filed Oct. 18, 2018, which is incorporated herein by reference in its entirety.

TECHNICAL FIELD

The present disclosure relates generally to methods, apparatuses, and systems that assist in the clearing of a patient's airway. More specifically, the present disclosure relates to methods, apparatuses, and systems that assist in aspirating the airway of a patient and where the apparatus is portable and able to be used with a single hand.

BACKGROUND

Airway injuries, which may result from blunt force and penetrating injuries to the neck and chest, can be life threatening conditions, particularly on a battlefield. The presence of concomitant severe injuries and non-specific symptoms and signs for this type of injury may delay diagnosis and lead to early fatal outcome due to asphyxiation from airway obstruction or death from tension pneumothorax, or late sequela such as airway stenosis and recurrent pulmonary infections.

Airway obstruction and compromise is the second leading cause of preventable battlefield death, which can be attributed to the unavailability of sufficiently powerful portable suction systems, among others factors. Therefore, prompt diagnosis is mandatory for the survival of these patients. However, treatment of these patients is similarly challenging: it includes securing a patient airway that will allow adequate ventilation and then repairing the injury with a smaller impact on the respiratory function and the quality of life of the patient.

A number of portable suction devices available in the market are either manually powered and less efficient, or battery powered and bulky/heavy for combat medics to carry in their kits. Examples of portable suction devices include the Laerdal Compact Suction Unit® 4 (LCSU® 4) by Laerdal Medical; the SSCOR Quickdraw® by SSCOR, Inc.; and the Clario Airway Suction Pump by Medela AG.

The LCSU® 4 includes a collection canister supported by a wire bracket. The collection canister can come in a 300 mL size or an 800 mL size container when extra suction volume is needed. The LCSU® 4 weighs between 3.3 to 4.3 pounds depending on the collection canister size and provides between 50 mmHg to 550 mmHg vacuum pressure for about 45 minutes when powered by batteries. The collection canister must also be correctly oriented to fit into the wire bracket. An air flow rate of 30 L/min can be obtained with the device. The overall dimensions of the LCSU® 4 are 18.5 cm×26.2 cm×8.12 cm with a 300 mL canister and 23.6 cm×19 cm×23.6 cm with an 800 mL canister.

The SSCOR Quickdraw® Tactical requires 10 AAA sized batteries to power the device for 60 to 100 minutes. A maximum negative pressure of >500 mmHg and a low negative pressure setting of 80 mmHg to 100 mmHg can be achieved with the device. The drainable collection canister can hold a maximum of 300 mL. The collection canister must also be correctly oriented. The SSCOR Quickdraw® Tactical weighs 2.6 pounds and has overall dimensions of 27 cm×11 cm×11 cm.

The Clario Airway Suction Pump by Medela AG is intended for home health use and can operate for about 50 minutes when powered using the rechargeable battery. A low vacuum setting of 135 mmHg, a medium vacuum setting of 270 mmHg, and a maximum vacuum setting of 600 mmHg can be achieved with the device. The collection canister can hold a maximum of 550 mL and must also be correctly oriented during operation. A fluid flow rate of 15 L/min can be obtained with the device. The Clario Airway Suction Pump weighs about 2.0 kilograms and has overall dimensions of 22.3 cm×25.5 cm×9.5 cm.

Market assessments and surveys conducted by the inventors have demonstrated that combat medics require a lightweight, compact, efficient, and reliable portable suction alternative for the battlefield because combat medics are required to carry everything on their backs. Similarly, civilian EMS providers need a lightweight, reliable, and effective means of clearing debris such as saliva and vomitus from the airway of critical patients. Thus, portability, effectiveness, and ruggedness are key attributes for an airway suction device.

Currently, such a device does not exist. Current designs are over twenty years old and fall short on many aspects because they were developed using poor/outdated technology. The designs are typically heavy, bulky, provide inadequate suction, and have a short battery life. This results in unnecessary patient suffering and can lead to death from suffocation due to inadequate aspiration of debris or the inability to gain control of the patient's airway in a timely manner.

In view of the foregoing, it is apparent that there exists a need for a device and method to clear airways of patients that overcomes, mitigates, or solves the above problems in the art. Embodiments described herein fulfill this and other needs in the art, which will become apparent to the skilled artisan once given the following disclosure.

SUMMARY

This disclosure includes implementations of methods and configurations of apparatuses and systems for aspirating the airway of a patient. Non-limiting examples of conditions that benefit from this disclosure include, but are not limited to, tracheobronchial injuries, asphyxiation from airway obstruction, and tension pneumothorax.

Certain embodiments are directed to an apparatus for aspirating an airway of a patient, the apparatus comprising: a main body comprising: a pressure sensor; a controller in communication with the pressure sensor, the controller comprising a processor, a centrifugal pump, and a memory; a power source in communication with the controller; a storage canister housing coupled to the main body, the storage canister housing comprising a first end coupled to the main body, a second end having a weighted portion and configured to be coupled to the first end to permit free rotation, such that the second end gravitationally rotates about a first longitudinal axis, an inlet disposed on the second end, where the inlet is configured to rotate about a second longitudinal axis that is offset by a distance from the first longitudinal axis; a storage canister disposed within the storage canister housing and coupled to the inlet of the storage canister housing; a suction tube having a proximal end coupled to the inlet and a distal end; and a handle coupled to the distal end of the suction tube, the handle comprising a first portion having an opening configured to receive a suction catheter, and a second portion moveably coupled to the first portion and configured to receive the distal end of the suction tube. The apparatus can further include a filter disposed within the opening of the first portion. In certain aspects, the apparatus of any embodiment described herein can be configured to include the first portion having a slot for receiving a release mechanism for detaching the second portion from the first portion. The controller can be configured to measure a pressure at the inlet and shut off the pump when the measured pressure falls below a threshold pressure. The apparatus of any embodiment described herein can further include a light source coupled to the handle. In certain aspects, the apparatus of any embodiment described herein can further include an outer cover configured to be coupled to the main body and enclose a portion of the storage canister housing. In certain aspects, the storage canister is configured to be at least partially collapsible, and in some instance fully collapsible. In certain aspects, filter(s) can be position at one or both ends of the canister to protect the pump from solid and viscous particles during suction and changes in orientation (see FIG. 17 for an example). The interior walls of the canister can be modified or coated, for example the interior wall of the canister can be coated, completely or partially with super absorbent polymers, pH reagents, and/or oxygen-sensitive luminescent materials that will assist with demobilizing fluid contents located inside for evacuation from device and assist with content characterization. Certain embodiments can include design elements that provide for characterization of fluid content, these elements include but are not limited to (i) a separate sample chamber couple to the canister, wither upstream or downstream with respect to the canister; (ii) sensors that measure metrics that help identify fluid sources, such as pH or blood oxygenation, this allows for determination if accumulated fluids include arterial blood (indicating a dangerous hemorrhage), vomit, or other components that may dictate clinical response; (iii) a multi-lumen tubing can be utilized to provide a conduit for wiring, etc. and/or (iv) a "periscope-like" orifice in the housing located over the canister for assisted viewing of canister content. In certain aspects, a suction device tubing with multi lumen tubing can include a suction catheter equipped with additional features without becoming large and bulky, the features include, but are not limited to (i) fiber optic cables inserted through a small channel of the tubing—eliminating the need for an LED, switch and a battery to be embedded into the catheter; and/or (ii) electrical controls and/or connections for the operation of the suction tip, this may also allow for small data lines to be passed through the small channel to transmit information to a CPU within the pump housing.

The centrifugal pump can be configured to generate a vacuum pressure of at least or about 400, 500, 600, 700, to 800 mmHg, including all values and ranges there between. The controller can be configured to evacuate water, vomitus, solid pieces, solid particulates, and/or blood at a flow rate of at least or about 0.5, 0.75, 1.0, 1.25, 1.5, 2.0, 3.0, 4.0, 5.0 to 10 L/min, including all values and ranges there between. The storage canister can have a storage volume of at least 0.2, 0.5, 1.0, 1.5, 2.0 L to 3.0 L. The processor can be configured to determine a patient condition via optical and/or electro-chemical analysis. The main body, storage canister housing, and/or outer cover includes a surface coating selected from the group of surface coating characteristics consisting of: anti-reflective, camouflage, electromagnetic shielding, and combinations thereof. The apparatus of any embodiment described herein can further include a muffler system coupled to the main body to reduce operating noise. The storage canister can have a fixed volume portion capable of holding up to 200, 300, 400, 500, 600, 700, 800, 900 mL or more, and an expandable volume portion capable of holding at least an additional 100, 200, 300, 400, 500 mL to 3000 mL or greater. The apparatus of any embodiment described herein can further include a suction tip attachment configured to be coupled to the suction catheter, where the suction tip attachment includes a filter for trapping debris. The controller can be configured to provide a pressure range for treating pneumothorax (e.g., 5 to 20 mmHg). The apparatus of any embodiment described herein can where the apparatus has an overall dimension of 15 cm×7.5 cm×7.5 cm to 30 cm×15 cm×15 cm. In certain instances the overall dimension is at most 30 cm×15 cm×15 cm. The apparatus of any embodiment described herein can have an overall weight of less than 0.5, 1.0, or 1.2 kg. The handle can further include a trigger mechanism configured to actuate the centrifugal pump. In certain aspects, the handle can include a lumen in fluid communication with an irrigation chamber and the controller configured to dispense fluid from the irrigation container through the lumen. The apparatus of any embodiment described herein can include a handle having a camera.

Certain embodiments are directed to an apparatus for aspirating an airway of a patient, the apparatus comprising a main body comprising, a pressure sensor, a controller in communication with the pressure sensor, the controller comprising: a processor, a centrifugal pump, and a memory; a power source in communication with the controller; a storage canister housing coupled to the main body, the storage canister housing comprising: a first end coupled to the main body, a second end having a weighted portion and configured to be coupled to the first end to permit free rotation, such that the second end gravitationally rotates about a first longitudinal axis, an inlet disposed on the second end, where the inlet is configured to rotate about a second longitudinal axis that is offset by a distance from the first longitudinal axis; a storage canister disposed within the storage canister housing and coupled to the inlet of the storage canister housing, the storage canister comprising: a first portion having a plurality of ribs defining a fixed volume; a second portion coupled to the first portion and defining a second volume; and a suction tube having a proximal end coupled to the inlet and a distal end; and a handle coupled to the distal end of the suction tube, the handle comprising: a first portion having an opening configured to receive a suction catheter; and a second portion moveably coupled to the first portion and configured to receive the distal end of the suction tube. The apparatus of embodiments described herein can further comprising a filter disposed within the opening of the first portion. The first portion can include a slot for receiving a release mechanism for detaching the second portion from the first portion. The controller can be configured to measure a pressure at the inlet and shut off the pump when the measured pressure falls below a threshold pressure, e.g., a drop in of 50%. The apparatus of any embodiment described herein can further include a light source coupled to the handle. In certain aspects, the apparatus of any embodiment described herein can include an outer cover configured to be coupled to the main body and enclose a portion of the storage canister housing. The storage canister is configured to be at least partially collapsible, and in some instances fully collapsible. The apparatus of any embodiment described herein can where the centrifugal pump is configured to generate a vacuum pressure of at least 500, 600, 700, to 800 mmHg, including all values and ranges there between. The apparatus of any embodiment described herein can where the controller is configured to evacuate water, vomitus, and/or blood at a flow rate of at least 1.0, 1.25, 1.5, 2.0, 3.0, 4.0, 5.0 to 10 L/min, including all values and ranges there between. The storage canister can have a storage volume of at least 0.5 L. The storage volume can be 0.5, 1.0, 1.5, 2.0 L to 3.0 L or more. The processor can be configured to determine a patient condition via optical and/or electrochemical analysis. The main body, storage canister housing, and/or outer cover includes a surface coating selected from the group of surface coating characteristics consisting of: anti-reflective, camouflage, electromagnetic shielding, and combinations thereof. The apparatus of any embodiment described herein can further include a muffler system coupled to the main body to reduce operating noise. In certain aspects, the fixed volume of the first portion is at least 200, 300, 400, 500, 600, 700, 800, 900 mL or more, and an expandable volume portion capable of holding at least an additional 800, 900, 1000, 1100, 1500 mL, 2000 m, to 3000 mL or more. The apparatus of any embodiment described herein can further comprising a suction tip attachment configured to be coupled to the suction tip, where the suction tip attachment includes a filter for trapping debris. The controller can be configured to provide a pressure range for treating pneumothorax (e.g., 5 to 20 mmHg). The apparatus of any embodiment described herein can where the apparatus has an overall dimension of 15 cm×7.5 cm×7.5 cm to 30 cm×15 cm×15 cm. In certain instances the overall dimension is at most 30 cm×15 cm×15 cm. The apparatus of any embodiment described herein can weigh 0.5, 1.0, to 1.2 kg. In certain instances the apparatus weight is less than 1.2 kg. The apparatus of any embodiment described herein can where the handle further comprises a trigger mechanism configured to actuate the centrifugal pump. The handle can include or form a lumen in fluid communication with an irrigation chamber and the controller configured to dispense fluid from the irrigation container through the lumen. The handle can include a camera.

Certain embodiments are directed to methods for aspirating an airway of a patient, the method comprising: (a) providing any one of the apparatus described herein; (b) inserting the suction tube into the airway of the patient; (c) aspirating a fluid from the airway using any one of the apparatus described herein. The method can further include (e) detecting a patient condition via optical and/or electrochemical analysis using any one of the apparatus described herein.

The term "coupled" is defined as connected, although not necessarily directly, and not necessarily mechanically; two items that are "coupled" may be unitary with each other.

The terms "a" and "an" are defined as one or more unless this disclosure explicitly requires otherwise.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any configuration or implementation of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus, device, or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Any configuration or implementation of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the configurations described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the configurations depicted in the figures.

DESCRIPTION OF ILLUSTRATIVE EMBODIMENTS

Figure 1:
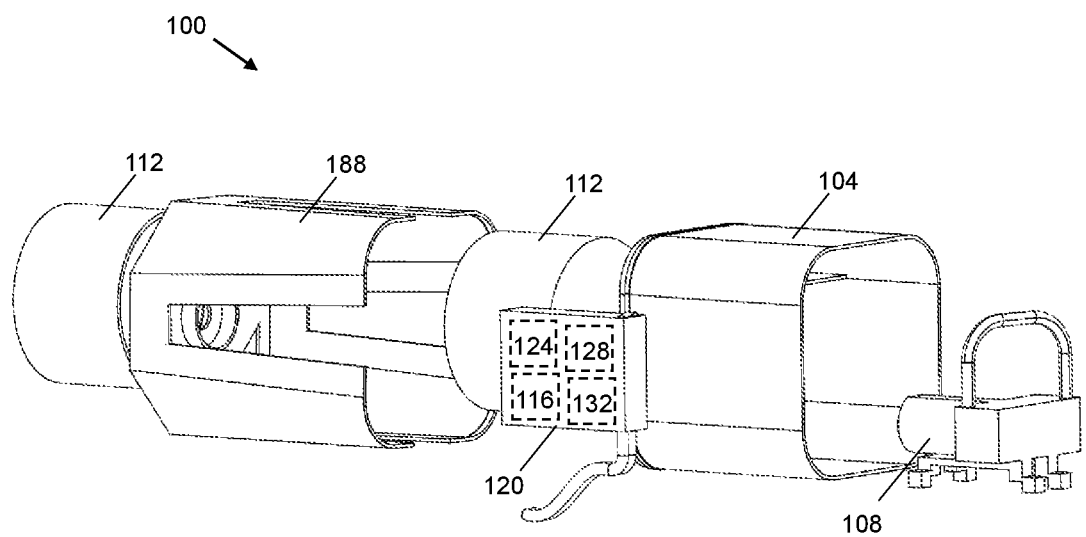
FIG. 1 shows an exploded view of an exemplary configuration of the present apparatus for aspirating an airway of a patient.
Figure 2:
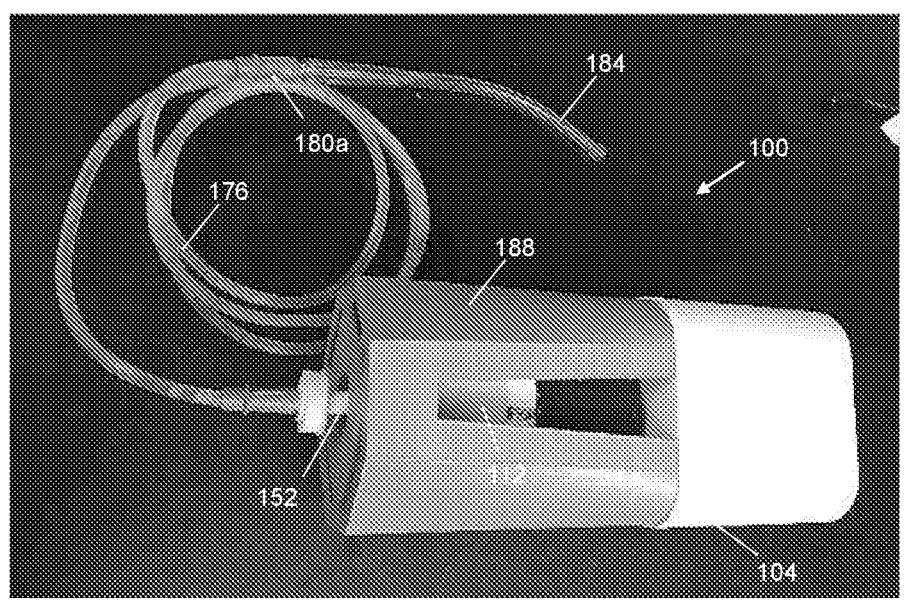
FIG. 2 shows a perspective view of a configuration of the present apparatus for aspirating an airway of a patient.
Figure 3:
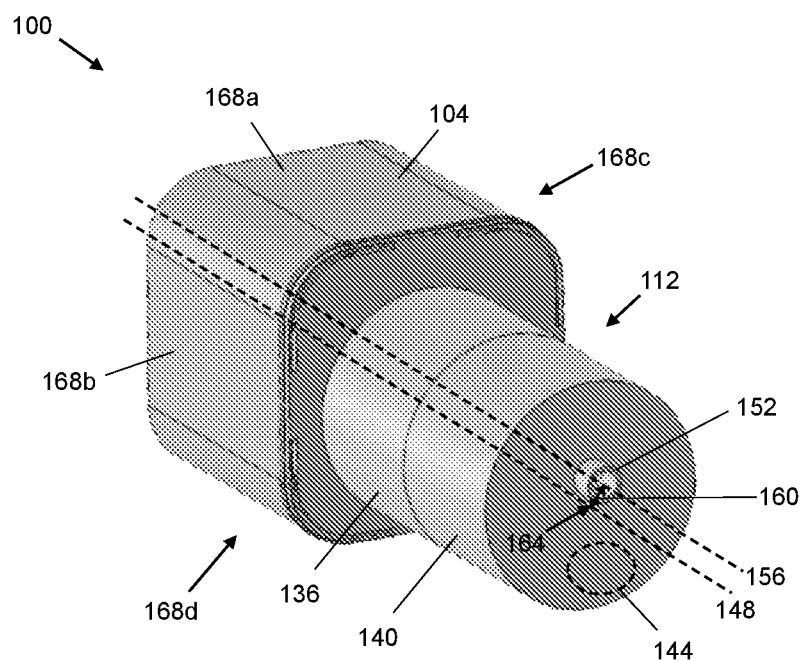
FIG. 3 shows a perspective view of a configuration of the storage canister housing coupled to the main body.
Figure 4A:
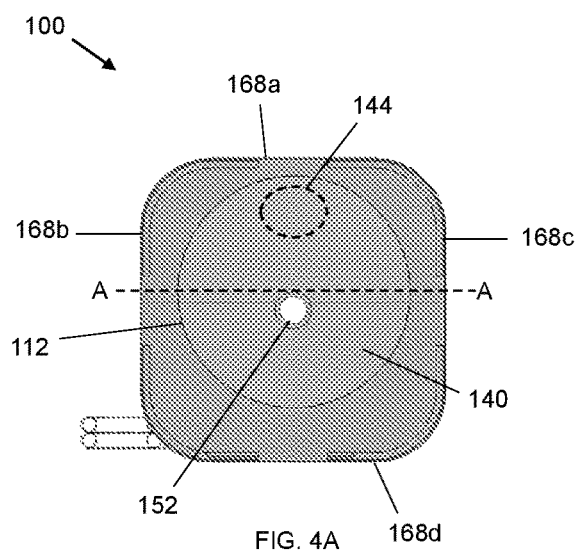
FIG. 4A shows an inlet end view of a configuration of the storage canister housing with the inlet in a first position.
Figure 4B:
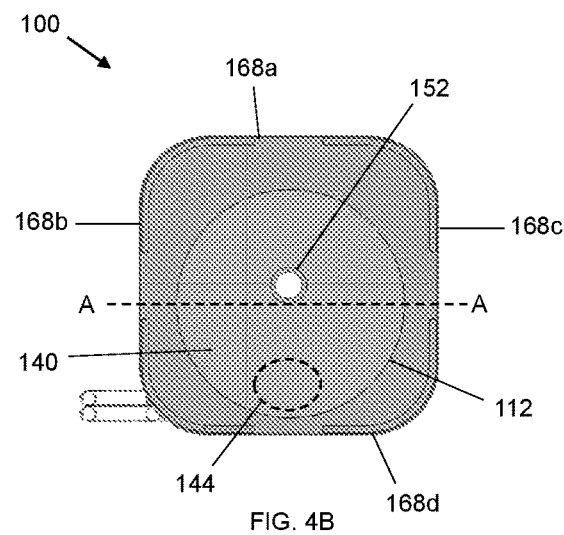
FIG. 4B shows the inlet end view of FIG. 4A with the inlet in a second position.

Referring now to the drawings, and more particularly to FIGS. 1-2, in some configurations an apparatus 100 for aspirating an airway of a patient includes a main body 104 having a pump 108 (e.g., centrifugal pump) and a storage canister housing 112 coupled to the main body 104. In some configurations, the pump 108 is configured to generate a vacuum pressure of at least 400 mmHg. The main body 104 can include a pressure sensor 116, a controller 120 in communication with the pressure sensor 116 and having a processor 124 and a memory 128, and a power source 132 in communication with controller 120. As shown in FIGS. 3 and 4A-4B, the storage canister housing 112 can include a first end 136 coupled to the main body 104, and a second end 140 having a weighted portion 144 and configured to be coupled to the first end 136 to permit free rotation, such that the second end 140 gravitationally rotates about a first longitudinal axis 148. In some configurations, the first end 136 can be coupled to the second end 140 with one or more sets of ball bearings to permit free rotation. An inlet 152 is disposed on the second end 140 and can be configured to rotate about a second longitudinal axis 156 that is offset by a distance 160 from the first longitudinal axis 148. In this way, an eccentric center of rotation 164 (with the center of rotation being along the inlet/outlet axis 156) permits the weighted portion 144 to orient the storage canister housing 112 using gravity such that the inlet 152 will move from a first position (as shown in FIG. 4A, inlet 152 is positioned below plane A-A bisecting storage canister housing 112) to a second position (as shown in FIG. 4B, inlet 152 has moved above plane A-A bisecting storage canister housing 112) when the apparatus 100 is placed on any one of its sides (e.g., 168a, 168b, 168c, 168d).

Figure 5:
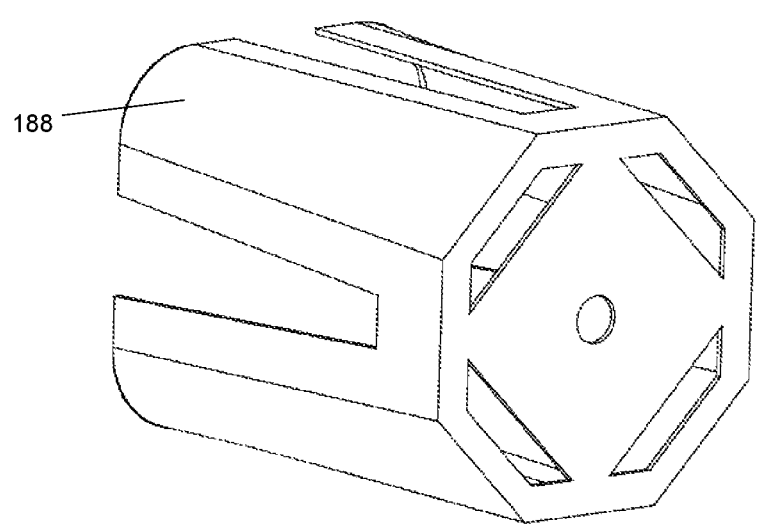
FIG. 5 shows a perspective view of an outer cover of the storage canister housing.
Figure 6:
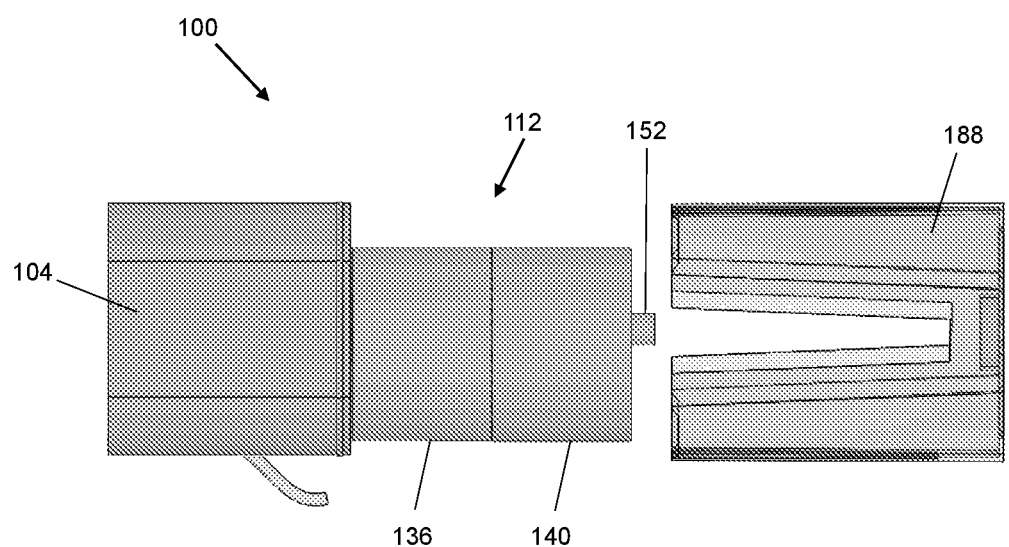
FIG. 6 shows a side view of FIG. 3 with an outer cover positioned to cover the storage canister housing.
Figure 7:
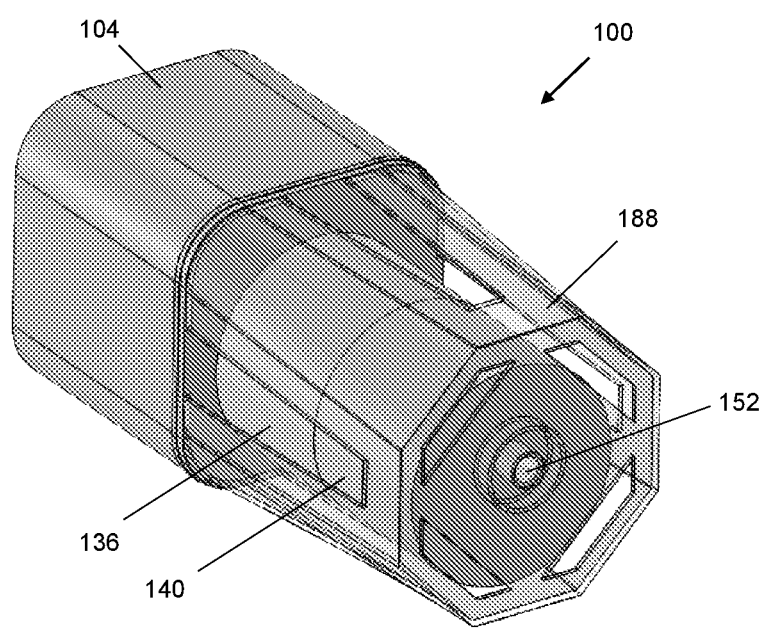
FIG. 7 shows a perspective view of the outer cover of FIG. 5 coupled to the main body.

As shown in FIGS. 3 and 4A-4B, storage canister housing 112 is cylindrical in shape, but can include other shapes configured to have an eccentric center of rotation with respect to the inlet. A storage canister (e.g. 172a, 172b, 172c, 172d) of in FIGS. 8-12, is disposed within the storage canister housing 112 and coupled to the inlet 152 of the storage canister housing 112. A suction tube 176 can be coupled to the inlet 152 and configured to receive a handle (e.g., 180a, 180b, 180c, 180d) that can be coupled to a suction catheter 184. In some configurations, a suction tip attachment (not shown) can be configured to be coupled to a distal end of the suction catheter 184, where the suction tip attachment includes a filter for trapping debris. In some configurations, such as the ones shown in FIGS. 2, 6 and 7, an outer cover 188 (as best shown in FIG. 5) can be configured to be coupled to the main body 104 and enclose a portion of the storage canister housing 112. As shown in FIG. 6, the outer cover 188 is aligned with the main body 104, and then placed over the storage canister housing 112 and coupled to the main body 104 to enclose a portion of the storage canister housing 112, as shown in FIG. 7.

In some configurations, the controller 120 is configured to measure a pressure at the inlet 152 and shut off the pump 108 when the measured pressure falls below a threshold pressure. In some configurations, the controller 120 is configured to evacuate water, vomitus, solid pieces, solid particulates, and/or blood at a flow rate of at least 0.5 L/min. In some configurations, the controller 120 is configured to provide a pressure range for treating pneumothorax. In some configurations, the processor 124 is configured to determine a patient condition via optical and/or electrochemical analysis.

Figure 8:
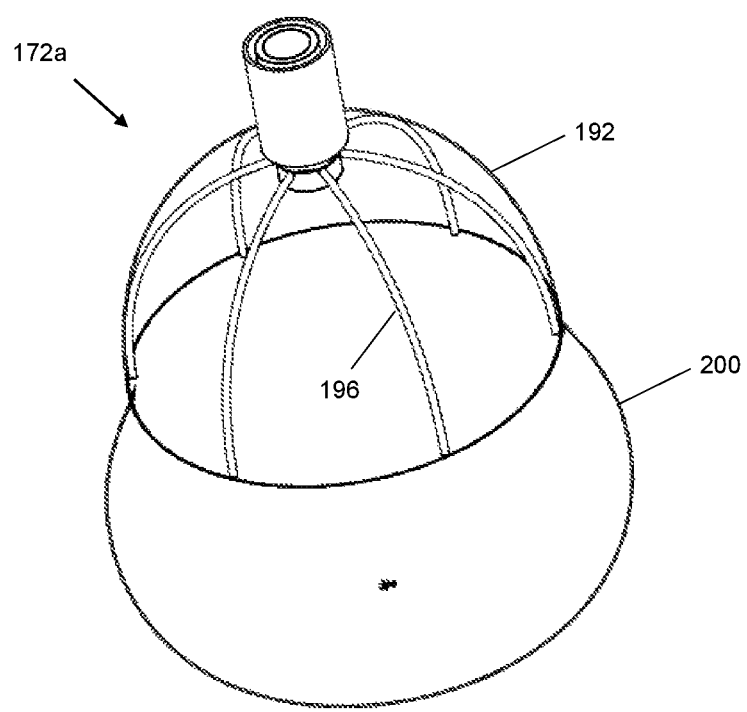
FIG. 8 shows a perspective view of an exemplary configuration of a storage container.
Figure 9:
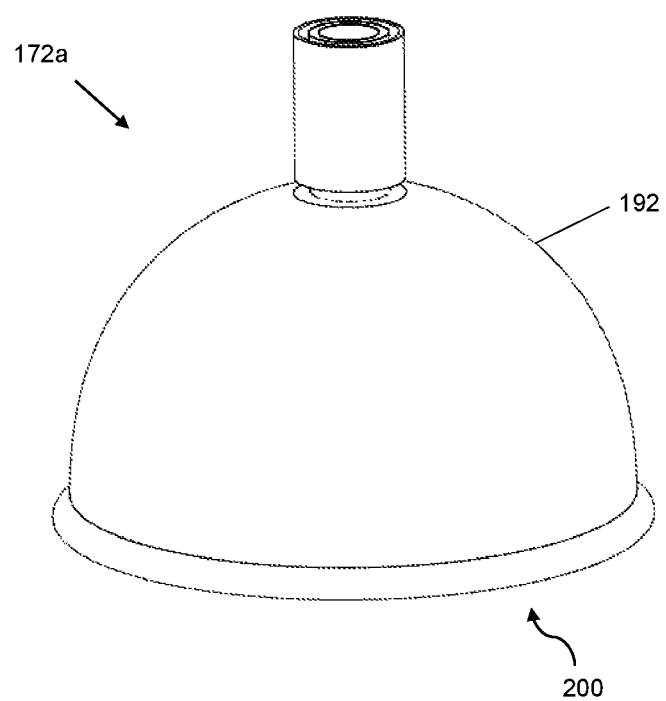
FIG. 9 shows the storage container of FIG. 8 in a collapsed state.
Figure 10:
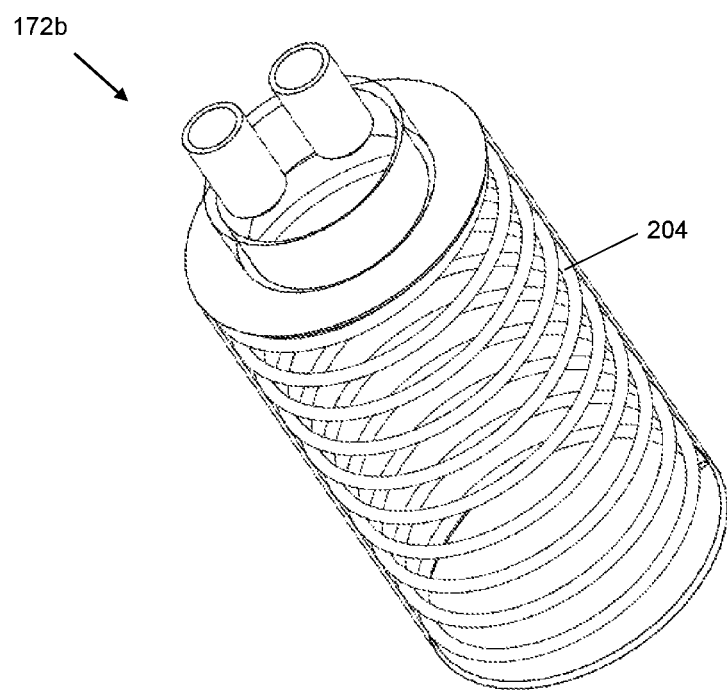
FIG. 10 shows a perspective view of a second configuration of a storage container.
Figure 11:
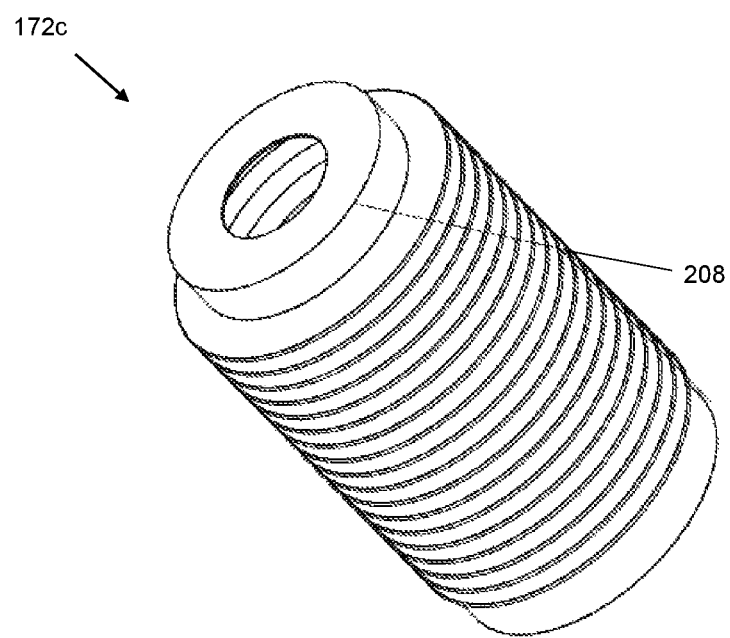
FIG. 11 shows a perspective view of a third configuration of a storage container.
Figure 12:
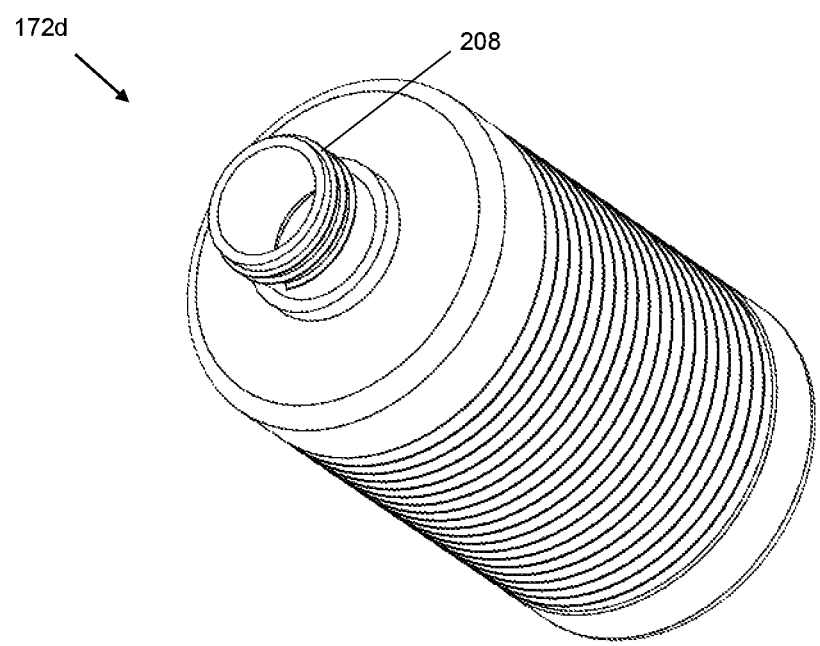
FIG. 12 shows a perspective view of a fourth configuration of a storage container.

As shown in FIGS. 8-12, in some configurations the storage canister (e.g., 172a, 172b, 172c, 172d) is configured to be at least partially collapsible. In this way, the overall dimensions of the apparatus can be minimized while providing the ability to hold sufficient fluid volume as needed. As shown in FIG. 8, in some configurations the storage canister 172a can include a first portion 192 having a plurality of ribs 196 defining a fixed volume and a second portion 200 coupled to the first portion 192 and defining a second volume. As shown in FIG. 9, the second portion 200 can collapse to be at least partially contained within the first portion 192 when not in use. In some configurations, the storage canister 172a has a total storage volume of at least 0.2 L. In some configurations, the storage canister 172a has a fixed volume portion capable of holding up to 200 mL, and an expandable second volume portion capable of holding at least an additional 100 mL. In some configurations, such as the one shown in FIG. 10, the storage canister 172b can include an internal spring coil 204 configured to gradually expand the storage canister 172b as fluid fills the storage canister 172b. In some configurations, such as the one shown in FIG. 11, the storage canister 172c can include a male end 208 configured to receive a female end (not shown). In some configurations, such as the one shown in FIG. 12, the male end 208 of storage canister 172d can be threaded.

Figure 13A:
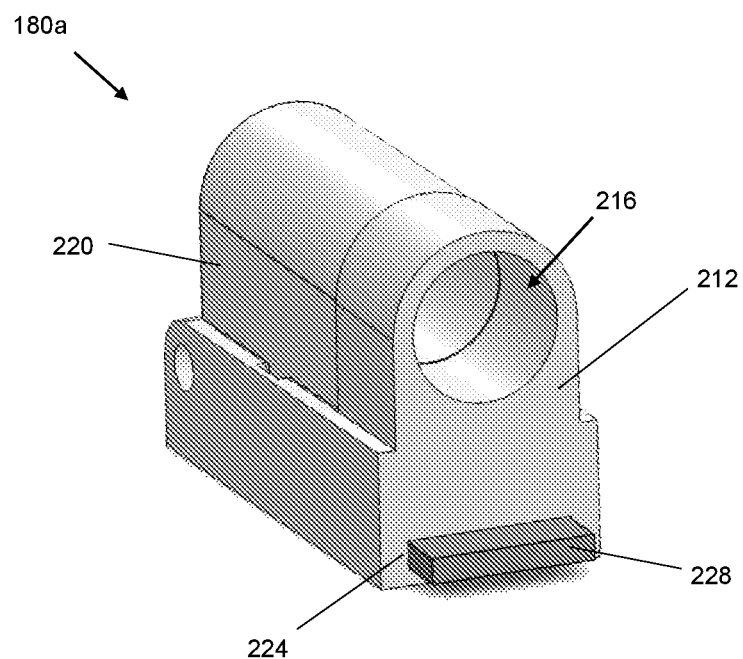
FIG. 13A shows a perspective view of a first configuration of a handle in a closed position with a key inserted into a release slot.
Figure 13B:
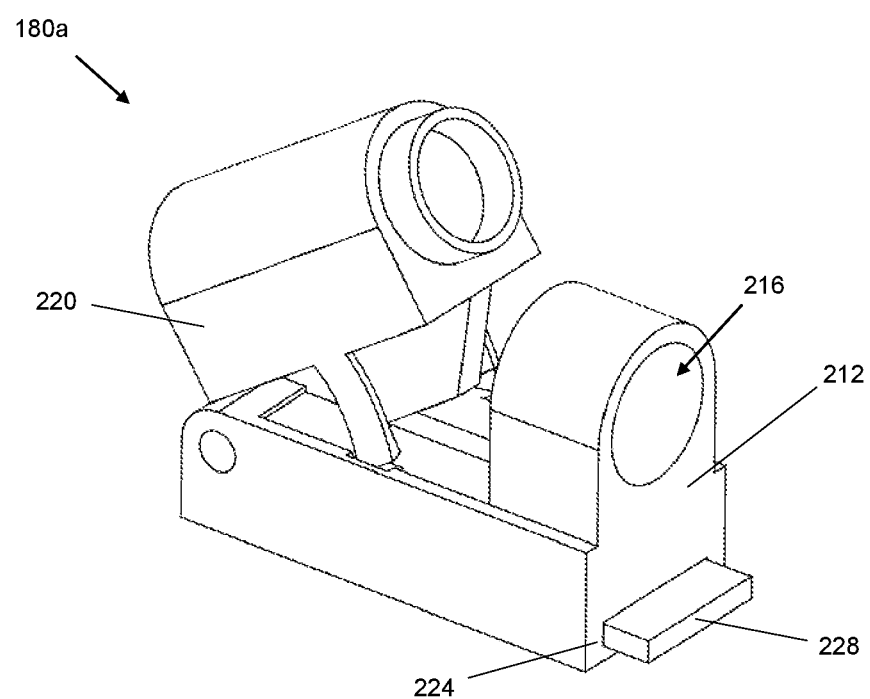
FIG. 13B shows a perspective view of the handle of FIG. 13A in an open position.
Figure 13C:
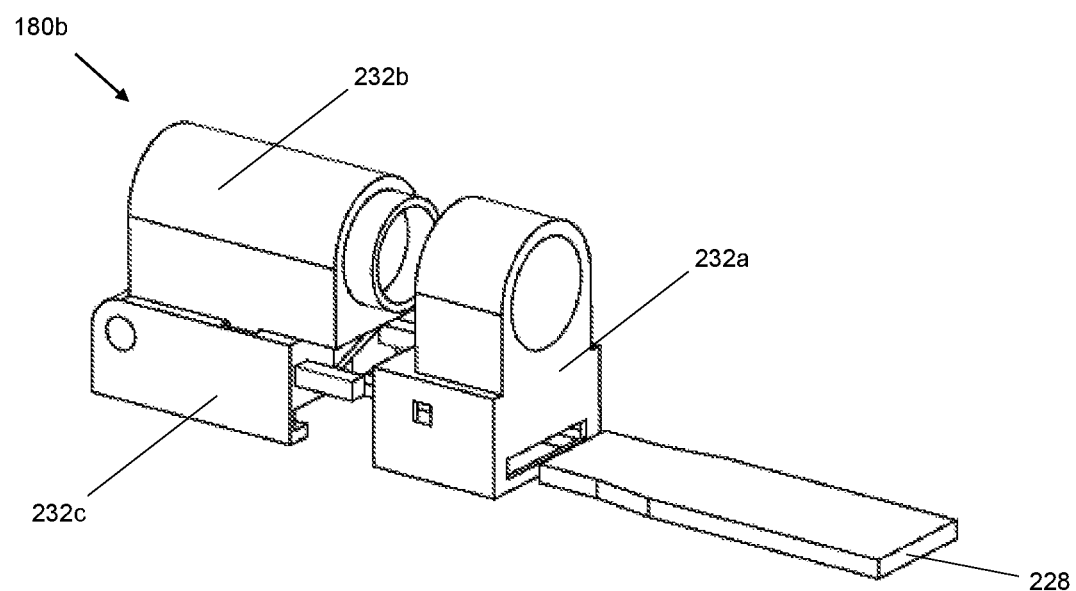
FIG. 13C shows an exploded perspective view of a second configuration of a handle.
Figure 14A:
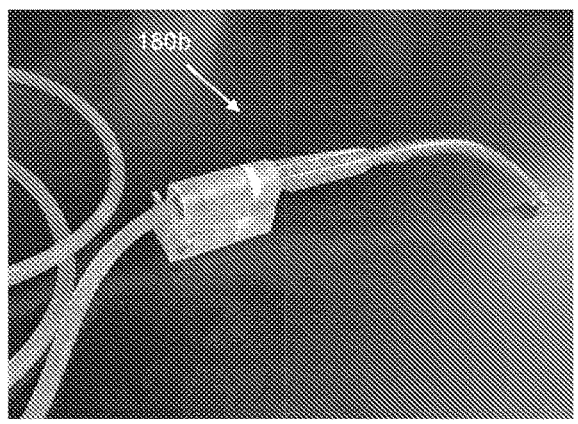
FIG. 14A shows a perspective view of a second configuration of a handle in a closed position and coupled to a suction catheter.
Figure 14B:
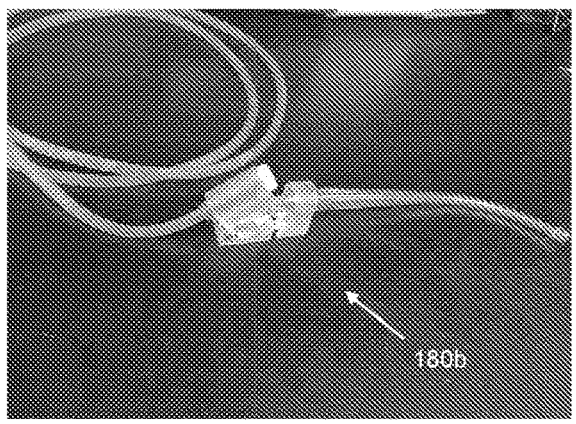
FIG. 14B shows a perspective view of the handle of FIG. 14A in an open position and coupled to a suction catheter.
Figure 15:
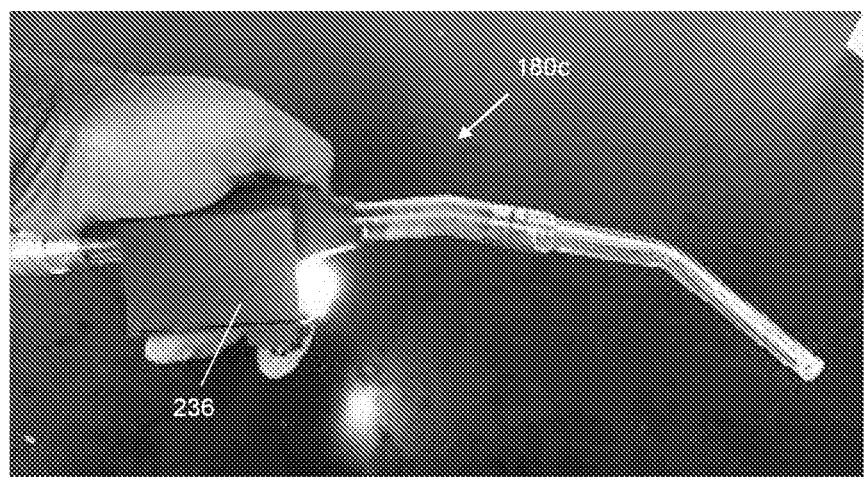
FIG. 15 shows a perspective view of a third configuration of a handle coupled to a light source.
Figure 16:
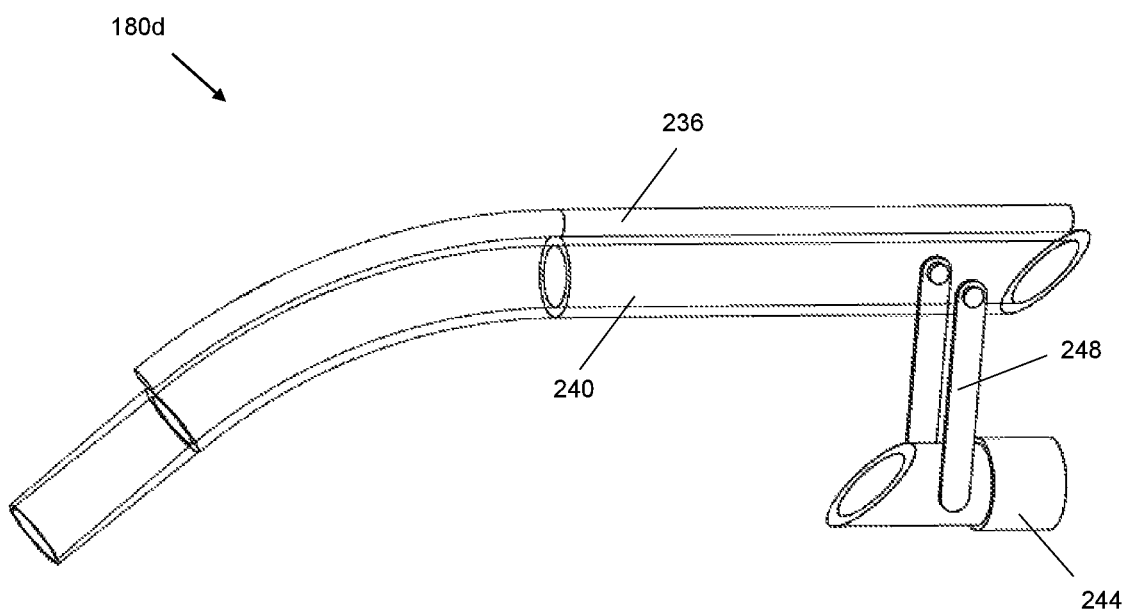
FIG. 16 shows a side view of a fourth configuration of the handle in an open position and coupled to a light source.
Figure 17:
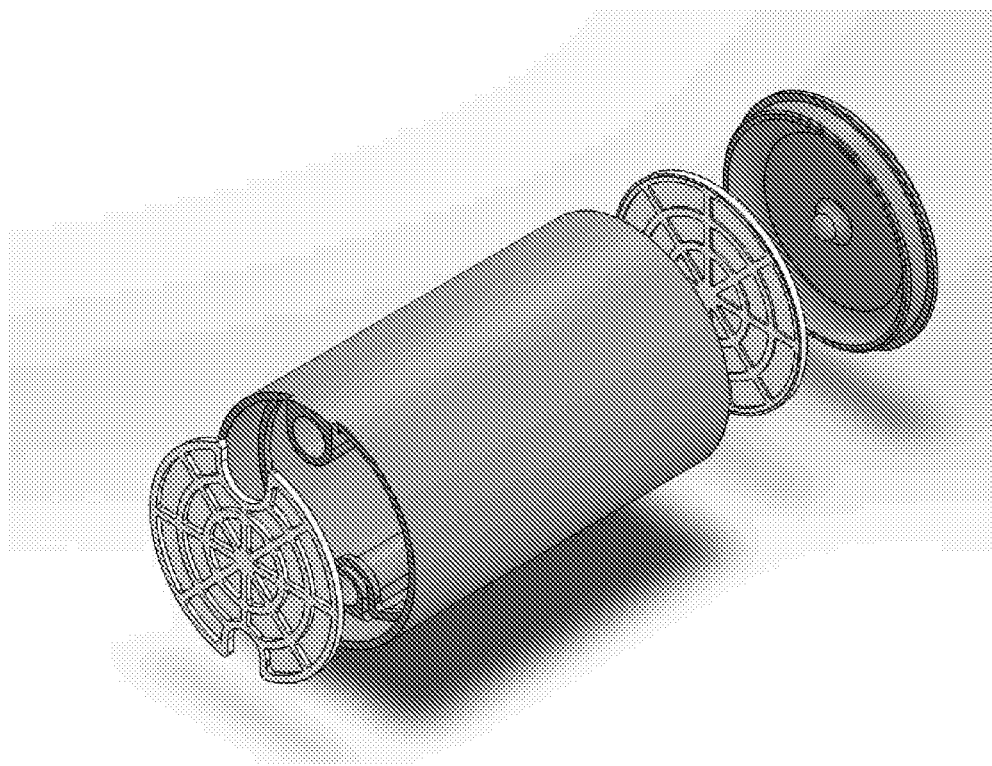
FIG. 17 shows an example of a canister comprising a filter at both ends.
Figure 18:
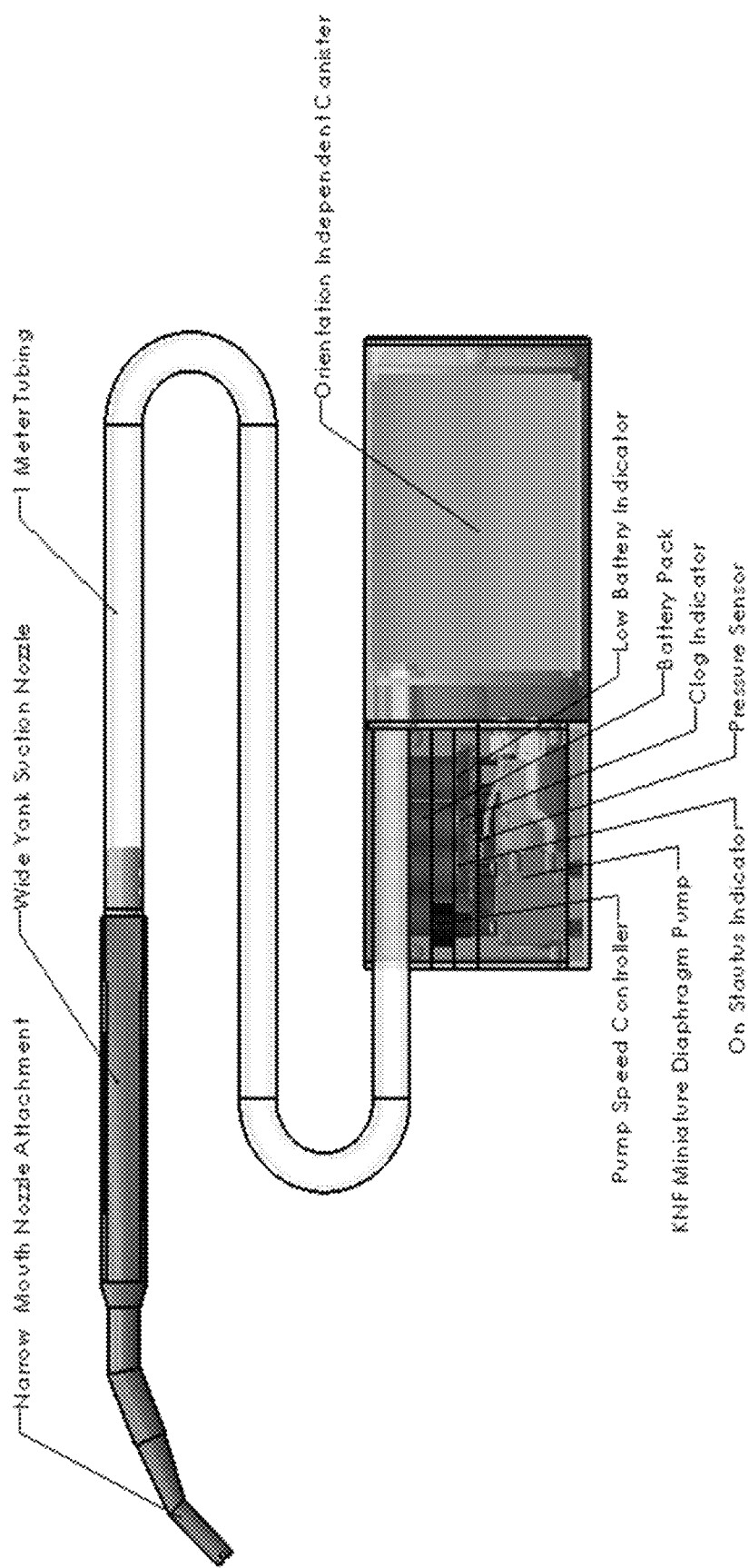
FIG. 18 shows one example of a device that is a shock resistant, low profile, noise dampening portable suction device.

As shown in FIGS. 13A-13B, in some configurations the aspirating apparatus includes a handle (e.g., 180a, 180b, 180c, 180d) having a first portion 212 that has an opening 216 configured to receive a suction catheter 184; and a second portion 220 moveably coupled to the first portion 212 and configured to receive the distal end of the suction tube 176. In some configurations, a filter is disposed within the opening 216 of the first portion 212 of the handle 180a. In some configurations, the first portion 212 includes a slot 224 for receiving a release mechanism (e.g., key 228) for decoupling the second portion 220 from the first portion 212. As best shown in FIG. 13A, when key 228 is inserted into the slot 224, the internal locking mechanism is disengaged to permit the second portion 220 to rotate from a closed position (as shown in FIGS. 13A and 14A) to an open position as shown in FIGS. 13B, 13C, and 14B. In this way, debris that gets trapped can be quickly removed and the handle 180a can be closed to resume suction. In some configurations, such as the one shown in FIG. 13C, the handle 180b can include two or more portions (e.g., 232a, 232b, 232c) that can be coupled together to form handle 180b. In this way, the handle 180b can be decoupled to remove larger pieces of debris and/or to more easily clean the handle 180b. In some configurations, such as the ones shown in FIGS. 15-16, a light source 236 can be coupled to the handle (e.g., 180c, 180d). As shown in FIG. 16, the handle 180d includes a first portion 240 coupled to the second portion 244 via a break-action type hinge 248. In some configurations, the handle includes a trigger mechanism configured to actuate the centrifugal pump. In some configurations, the handle includes a lumen in fluid communication with an irrigation chamber and the controller configured to dispense fluid from the irrigation container through the lumen. In some configurations, the handle includes an integrated camera.

In some configurations, the main body 104, storage canister housing 112, and/or outer cover 188 includes a surface coating selected from the group of surface coating characteristics consisting of: anti-reflective, camouflage, electromagnetic shielding, and combinations thereof.

In some configurations, a muffler system can be coupled to the main body to reduce operating noise.

In some configurations, the apparatus has an overall dimension of 30 cm×15 cm×15 cm or less. In some configurations, the apparatus has an overall weight of less than 1.2 kg.

In some implementations, a method for aspirating an airway of a patient includes (a) providing any one of the present apparatuses; (b) inserting the suction tube into the airway of the patient; (c) aspirating a fluid from the airway using any one of the present apparatuses. In some implementations, the method further includes detecting a patient condition via optical and/or electrochemical analysis using any one of the present apparatuses.

The above specification and examples provide a complete description of the structure and use of exemplary configurations. Although certain configurations have been described above with a certain degree of particularity, or with reference to one or more individual configurations, those skilled in the art could make numerous alterations to the disclosed configurations without departing from the scope of this invention. As such, the various illustrative configurations of the present devices, apparatuses, kits, and methods are not intended to be limited to the particular forms disclosed. Rather, they include all modifications and alternatives falling within the scope of the claims, and configurations other than the one shown may include some or all of the features of the depicted configuration. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one configuration or may relate to several configurations.

The claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

1. C. Prokakis, et al. "Airway trauma: A review on epidemiology, mechanisms of injury, diagnosis and treatment" Journal of Cardiothoracic Surgery, 9(1):117, 2014.
2. Eastridge, B. J., et al, "Death on the battlefield (2001-2011): Implications for the future of combat casualty care" J Trauma & Acute Care Surg, 73(6), S431-S437, 2012.
3. Peake J B. "Beyond the Purple Heart: continuity of care for the wounded in Iraq" N Engl J Med, 352(3):219-222, 2005.
4. Champion H R, et al, "A profile of combat injury". J Trauma, 54(5):513-519, 2003.
5. A. T. Simpson. "Transporting lazarus: Physicians, the state, and the creation of the modern paramedic and ambulance 1955-73." J History of Medicine & Allied Sciences, 2013.
6. Calkins, M. D. "Evaluation of possible battlefield suction pumps for the far-forward setting." Military medicine, 167(10): 803, 2002.

The invention claimed is:

1. An apparatus for aspirating an airway of a patient, the apparatus comprising:
 a main body comprising:
  a pressure sensor;
  a controller in communication with the pressure sensor, the controller comprising:
   a processor;
   a centrifugal pump; and
   a memory;
  a power source in communication with the controller;
 a storage canister housing coupled to the main body, the storage canister housing comprising:
  a first end coupled to the main body;
  a second end having a weighted portion and configured to be coupled to the first end to permit free rotation, such that the second end gravitationally rotates about a first longitudinal axis;
  an inlet disposed on the second end, where the inlet is configured to rotate about a second longitudinal axis that is offset by a distance from the first longitudinal axis;
 a storage canister disposed within the storage canister housing and coupled to the inlet of the storage canister housing;
 a suction tube having a proximal end coupled to the inlet and a distal end; and
 a handle coupled to the distal end of the suction tube, the handle comprising:
  a first portion having an opening configured to receive a suction catheter; and
  a second portion moveably coupled to the first portion and configured to receive the distal end of the suction tube.

2. The apparatus of claim 1, further comprising a filter disposed within the opening of the first portion.

3. The apparatus of claim 1, where the first portion includes a slot for receiving a release mechanism for detaching the second portion from the first portion.

4. The apparatus of claim 1, where the controller is configured to measure a pressure at the inlet and shut off the pump when the measured pressure falls below a threshold pressure.

5. The apparatus of claim 1, further comprising a light source coupled to the handle.

6. The apparatus of claim 1, further comprising an outer cover configured to be coupled to the main body and enclose a portion of the storage canister housing.

7. The apparatus of claim 1, where the storage canister is configured to be at least partially collapsible.

8. The apparatus of claim 1, where the centrifugal pump is configured to generate a vacuum pressure of at least 400 mmHg.

9. The apparatus of claim 1, where the controller is configured to evacuate water, vomitus, solid pieces, solid particulates, and/or blood at a flow rate of at least 0.5 L/min.

10. The apparatus of claim 1, where the storage canister has a storage volume of at least 0.2 L.

11. The apparatus of claim 1, where the processor is configured to determine a condition of the patient via optical and/or electrochemical analysis.

12. The apparatus of claim 1, where the main body, the storage canister housing, and/or an outer cover includes a surface coating selected from a group of surface coating characteristics consisting of: anti-reflective, camouflage, electromagnetic shielding, and combinations thereof.

13. The apparatus of claim 1, further comprising a muffler system coupled to the main body to reduce operating noise.

14. The apparatus of claim 1, where the storage canister has a fixed volume portion capable of holding up to 200 mL, and an expandable volume portion capable of holding at least an additional 100 mL.

15. The apparatus of claim 1, further comprising a suction tip attachment configured to be coupled to the suction catheter, where the suction tip attachment includes a filter for trapping debris.

16. The apparatus of claim 1, where the controller is configured to provide a pressure range for treating pneumothorax.

17. The apparatus of claim 1, where the apparatus has an overall dimension of 30 cm×15 cm×15 cm or less.

18. The apparatus of claim 1, where the apparatus has an overall weight of less than 1.2 kg.

19. A method for aspirating an airway of a patient, the method comprising:
(a) providing the apparatus of claim 1;
(b) inserting the suction tube into the airway of the patient; and
(c) aspirating a fluid from the airway using the apparatus of claim 1.

20. An apparatus for aspirating an airway of a patient, the apparatus comprising:
a main body comprising:
a pressure sensor;
a controller in communication with the pressure sensor, the controller comprising:
a processor;
a centrifugal pump; and
a memory;
a power source in communication with the controller;
a storage canister housing coupled to the main body, the storage canister housing comprising:
a first end coupled to the main body;
a second end having a weighted portion and configured to be coupled to the first end to permit free rotation, such that the second end gravitationally rotates about a first longitudinal axis;
an inlet disposed on the second end, where the inlet is configured to rotate about a second longitudinal axis that is offset by a distance from the first longitudinal axis;
a storage canister disposed within the storage canister housing and coupled to the inlet of the storage canister housing, the storage canister comprising:
a first portion having a plurality of ribs defining a fixed volume;
a second portion coupled to the first portion and defining a second volume; and
a suction tube having a proximal end coupled to the inlet and a distal end; and
a handle coupled to the distal end of the suction tube, the handle comprising:
a first portion having an opening configured to receive a suction catheter; and
a second portion moveably coupled to the first portion and configured to receive the distal end of the suction tube.

* * * * *